United States Patent [19]

Heath-Brown

[11] 3,989,717

[45] Nov. 2, 1976

[54] INDOLOBENZAZEPINE DERIVATIVES

[75] Inventor: Basil Heath-Brown, Welwyn Garden City, England

[73] Assignee: Hoffmann-La Roche Inc., Nutley, N.J.

[22] Filed: Mar. 17, 1975

[21] Appl. No.: 559,118

[30] Foreign Application Priority Data

Mar. 25, 1974 United Kingdom............... 13207/74

[52] U.S. Cl. ...................... 260/326.85; 260/239 D; 260/293.55; 260/313.1; 260/326.27; 260/326.31; 260/326.9; 424/274
[51] Int. Cl.² ...................................... C07D 487/06
[58] Field of Search ................. 260/326.27, 326.31, 260/326.85, 326.9

[56] References Cited
OTHER PUBLICATIONS

Wagner et al., *Synthetic Organic Chemistry* (1953) pp. 7,675–7,676.
*Chem. Abs.* vol. 60: 2916, (1963) abs. of Brit. Pat. 936,783.

*Primary Examiner*—Nicholas S. Rizzo
*Assistant Examiner*—Mary C. Vaughn
*Attorney, Agent, or Firm*—Samuel L. Welt; Frank P. Hoffman

[57] ABSTRACT

Indolobenzazepine derivatives of the general formula

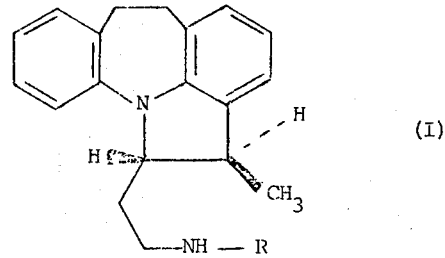

wherein R represents a methyl or ethyl group, and acid addition salts thereof are provided together with processes therefor.

The indolobenzazepine derivatives provided by the present invention possess an interesting anti-depressant activity which is not accompanied by undesirable cataleptic side-effects. They may accordingly be used as anti-depressant agents.

5 Claims, No Drawings

INDOLOBENZAZEPINE DERIVATIVES

DETAILED DESCRIPTION OF THE INVENTION

The present invention is concerned with indolobenzazepine derivatives and a process for the manufacture thereof.

The indolobenzazepine derivatives provided by the present invention are compounds of the general formula

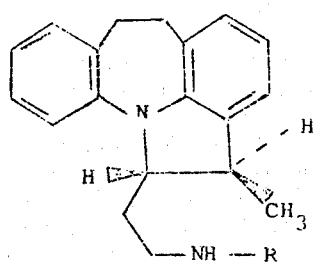

(I)

wherein R represents a methyl or ethyl group, and acid addition salts thereof.

The indolobenzazepine derivatives provided by the present invention possess an interesting anti-depressant activity which is not accompanied by undesirable cataleptic side-effects. They may accordingly be used as anti-depressant agents.

According to the process provided by the present invention, the indolobenzazepine derivatives aforesaid (i.e. the compounds of formula I and their acid addition salts) are manufactured by a. reducing a compound of the general formula

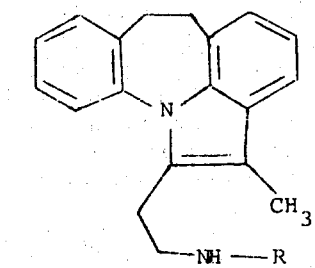

wherein R has the significance given earlier, or
b. Subjecting a compound of the general formula

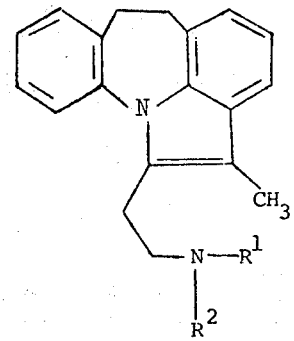

(III)

wherein $R^1$ and $R^2$ both represent a methyl group or both represent an ethyl group,
or a mixture of a compound of formula III and a compound of the general formula

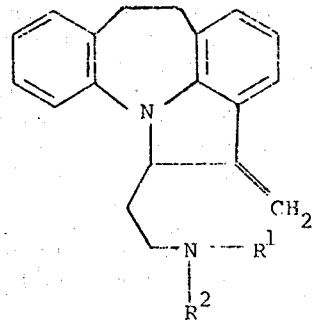

(IV)

wherein $R^1$ and $R^2$ have the significance given earlier, to reduction and de-methylation or de-ethylation in either sequence, and, if desired, converting the product obtained into an acid addition salt.

The starting materials of formula II used in embodiment (a) of the process can be prepared according to two methods.

In one method, N-amino-iminodibenzyl of the formula or an acid addition salt thereof is first reacted with methyl ethyl ketone to give the compound of the formula

VI

This reaction is suitably carried out in an inert organic solvent such as a lower alkanol (e.g., methanol, ethanol etc.), at normal pressure and at an elevated temperature. It is expedient to carry out this reaction at or near the reflux temperature of the reaction mixture. When an acid addition salt of N-amino-iminodibenzyl is used in the reaction, a hydrohalide, particularly the hydrochloride is preferred. When the reaction is carried out using N-amino-iminodibenzyl itself, it is preferred to include in the reaction mixture an acid, particularly a hydrohalic acid and especially hydrochloric acid.

In the next step, the compound of formula VI is converted into a compound of the general formula

VII wherein $R^3$ and $R^4$ both represent a methyl group or both represent an ethyl group or $R^3$ represents a methyl or ethyl group and $R^4$ represents a benzyl group, by reaction with formaldehyde and an amine of the general formula $$HN\begin{matrix}R^3\\R^4\end{matrix}$$  VIII wherein $R^3$ and $R^4$ have the significance given earlier. This reaction is carried out under the conditions of a MANNICH reaction as modified by THESING and SEMMLER (Annalen, 1964, 680, 52).

The starting materials of formula II are obtained from the compounds of formula VII by removing the substituent denoted by $R^4$. This can be carried out, when $R^4$ represents a benzyl group, by catalytic hydrogenation. Suitable hydrogenation catalysts for this purpose are palladium catalysts (e.g., palladium-on-carbon). The catalytic hydrogenation is conveniently carried out in a lower alkanol (e.g., methanol or ethanol), although any other solvent which is inert under the conditions of the catalytic hydrogenation can also be used. It is advantageous to carry out the catalytic hydrogenation at room temperature and atmospheric pressure. When $R^4$ in the compounds of formula VII represents a methyl or ethyl group, this group can be removed by reaction with a haloformic acid lower alkyl ester, preferably ethyl chloroformate, and treatment of the product with an alkali metal hydroxide. The reaction with a haloformic acid lower alkyl ester is expediently carried out using an excess of said ester and in the presence of an inert organic solvent such as an aromatic hydrocarbon (e.g., benzene, toluene, o-, m or p-xylene). Any other solvent which is inert under the conditions of the reaction can, however, also be used. This reaction is preferably carried out at an elevated temperature, particularly at a temperature at or near the reflux temperature of the reaction mixture. The resulting product, a urethane, is then treated with an alkali metal hydroxide to give a desired starting material of formula II. Potassium hydroxide is the preferred alkali metal hydroxide, but sodium hydroxide can also be used. This treatment is expediently carried out in a water-miscible inert organic solvent such as a lower alkanol (e.g., methanol or ethanol). It is also expedient to carry out this treatment at an elevated temperature under pressure (e.g., in a closed vessel).

The second method for the preparation of the starting materials of formula II comprises reacting N-amino-imino-dibenzyl of formula V hereinbefore, or preferably, an acid addition salt thereof such as the hydrochloride, with 1,3-dimethyl-3-piperidone and cyclizing the hydrazone formed by treatment with an acidic agent. A suitable solvent for the reaction is a lower alkanol (e.g., methanol or ethanol), but any other solvent which is inert under the conditions of the reaction can also be used. The cyclization is preferably carried out by treating the reaction mixture without isolation of the hydrazone with hydrogen chloride in a lower alkanol (e.g., ethanolic hydrogen chloride), although other acidic agents can also be used. For example, dry hydrogen chloride can be passed through the hot reaction mixture. Alternatively, although this is by no means as convenient, the hydrazone may be isolated from the reaction mixture and cyclized by treatment with a strong organic acid (e.g., a lower alkanecarboxylic acid) or an inorganic acid (e.g., sulfuric acid or phosphoric acid). When an inorganic acid is used, the cyclization is advantageously carried out in an inert organic solvent such as a lower alkanol.

The reduction of a starting material of formula II in accordance with embodiment (a) of the present process is preferably carried out using sodium in a mixture of tetrahydrofuran and liquid ammonia. Acidic reductions (e.g., using zinc and hydrochloric acid) can be used, but in these cases lower yields are generally obtained.

The starting materials of formulae III and IV used in embodiment (b) of the process can be prepared from compounds of the general formula

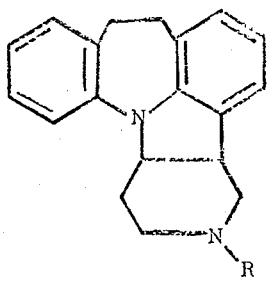

IX wherein R has the significance given earlier.

In a first step, a compound of formula IX is quaternized with a methyl halide (e.g., methyl iodide) when R represents a methyl group or an ethyl halide (e.g., ethyl iodide) when R represents an ethyl group. This quaternization is carried out according to conventional techniques.

The resulting quaternary salt is then subjected to a HOFMANN elimination reaction in accordance with methods known per se; for example, by treatment in a water miscible organic solvent such as a lower alkanol with silver oxide followed by application of heat to the resulting quaternary hydroxide in vacuo. According to this procedure there is obtained a mixture of starting materials of formula III and IV. As mentioned earlier, this mixture can be used in embodiment (b) of the process. However, the mixture can, if desired, be treated with acid (e.g., ethanolic hydrogen chloride), whereby there is obtained only a compound of formula III.

It will be appreciated that the compounds of formulae III and IV need not be isolated in pure form, but that they can be used in situ in embodiment (b) of the present process. It will also be appreciated that the compounds of formula VII hereinbefore in which $R^3$ and $R^4$ both represent a methyl group or both represent an ethyl group correspond to the compounds of formula III.

The reduction and de-methylation or de-ethylation of a compound of formula III or a mixture of a compound of formula III and a compound of formula IV in accordance with embodiment (b) of the process can, as mentioned earlier, be carried out in either sequence. The reduction can be carried out in the same manner as described earlier in connection with the reduction of a compound of formula II. The de-methylation or de-ethylation can be carried out in the same manner as described earlier in connection with the de-methylation or de-ethylation of a compound of formula VII. There is thus obtained a compound of formula I.

Alternatively, a compound of formula I can be obtained by hydrolytically removing the group COOX in a urethane of the formula

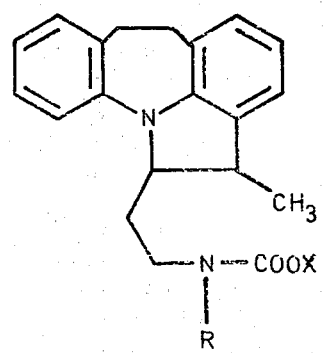

X wherein R has the significance given earlier and X represents a lower alkyl group.

The removal of the group COOX in a urethane of formula X can e.g. be effected by treating this urethane with an alkali metal hydroxide, preferably potassium hydroxide, although sodium hydroxide can also be used. The treatment with an alkali metal hydroxide is expediently carried out in a water-miscible inert organic solvent such as a lower alkanol, e.g. methanol or ethanol. It is also expedient to carry out this treatment at an elevated temperature under pressure, e.g. in a closed vessel.

For the preparation of a starting material of formula X, a compound of formula III or a mixture of such a compound and a compound of formula IV which, as indicated above, needs not to be isolated in pure form, is reacted with a haloformic acid lower alkyl ester, preferably ethyl chloroformate. This reaction is carried out in the same manner and under the same conditions as described earlier in connection with the removal of a methyl or ethyl group $R^4$ from a compound of formula VII.

The starting materials of formulae II and X are novel compounds.

An example of a compound of formula II is:
6,7-dihydro-2-methyl-1-(2-methylaminoethyl)-indolo[1,7-ab][1]benzazepine.

Examples of compounds of formula X are:

1-[2-(N-ethoxycarbonyl-N-methylamino)-ethyl]-1,2,6,7-tetrahydro-2-methylindolo[1,7-ab][1]benzazepine and
1-[2-(N-ethoxycarbonyl-N-ethylamino)-ethyl]-1,2,6,7-tetrahydro-2-methylindolo[1,7-ab][1]benzazepine.

The compounds of formula I form acid addition salts by treatment with inorganic acids (e.g., hydrhalic acids such as hydrochloric acid and hydrobromic acid, sulfuric acid, phosphoric acid, etc.) and with organic acids (e.g., citric acid, tartaric acid, malic acid, maleic acid, oxalic acid, methane-sulfonic acid, etc.). The pharmaceutically acceptable acid addition salts are preferred.

The compounds of formula I and their pharmaceutically acceptable acid addition salts can be used in medicine in the form of pharmaceutical preparations which contain them in association with a compatible pharmaceutical carrier, namely an organic or inorganic inert carrier material suitable for enteral (e.g., oral) or parenteral administration. Examples of such carrier materials are water, gelatin, lactose, starch, talc, magnesium stearate, gums, vegetable oils and petroleum jelly. The pharmaceutical preparations can be made up in a solid form (e.g., as tablets, capsules, dragees or suppositories) or in a liquid form (e.g., as solutions, emulsions or suspensions). The pharmaceutical preparations may be sterilized and/or may contain compatible adjuvants such as preservatives, stabilizing agents, flavoring agents, coloring agents, emulsifying agents, salts for varying the osmotic pressure or buffering agents.

The following Examples illustrate the process provided by the invention.

EXAMPLE 1

A. Preparation of the starting material:

14.5 g (0.05 mol) of 1,2,3,4,4a,8,9,14a-octahydro-3-methylpyrido[4',3':2,3]indolo[1,7-ab][1]benzazepine in 145 ml of benzene were treated with 3.8 ml (excess) of methyl iodide at 20° C. After 1 hour, the resulting methiodide was filtered off and the liquors were evaporated to a smaller volume, treated with a further 0.5 ml of methyl iodide and boiled under reflux for a short time. A second small crop of the methiodide was obtained. Total yield 21.6 g (100%); melting point 251°–252° C.

20.7 g (0.0479 mol) of the methiodide previously prepared were stirred with 207 ml of ethanol and 207 ml of water at 75°–80° C and treated with silver oxide (prepared from 20.4 g [2.5 × 0.0479 mol] of silver nitrate). After 1 hour, the solid material was filtered off and washed with ethanol/water (1:1); the strongly alkaline filtrate was evaporated in vacuo and the residue heated at 120° C/0.2 mm Hg to give 10.4 g of a pale-yellow syrup. The syrup was chromatographed over 200 g of alumina using benzene as the eluent. Partially purified material was obtained in the first six 100 ml fractions which were combined and evaporated to yield 6.4 g of a syrup. This syrup was dissolved in petroleum ether, passed through 5–10 g of alumina, evaporated and distilled from a msall retort. There were obtained 4.5 g of a material [boiling point ca 160° C (air-bath temperature) at $10^{-5}$ mm Hg] which formed a pale-yellow viscous syrup with a greenish-blue fluorescence. This syrup was a mixture of 1-(2-dimethylaminoethyl)-6,7-dihydro-2-methylindolo[1,7-ab]-[1]benzazepine and 1-(2-dimethylaminoethyl)-1,2,6,7-tetrahydro-2-methylene-indolo[1,7-ab][1]benzazepine.

B. The process:

The mixture of bases obtained according to part A of this Example can be converted into the trans-1,2,6,7-tetrahydro-2-methyl-1-(2-methylaminoethyl)indolo[1,7-ab][1]-benzazepine [boiling point 144°–152° C/$10^{-4}$ to $10^{-5}$ mm Hg] in the same manner as described in part B of Example 2. The hydrochloride melted at 198°–200° C.

EXAMPLE 2

A. Preparation of the starting material:

117 g (0.403 mol) of the methiodide obtained according to the first paragraph of Example 1 were stirred with 900 ml of ethanol and 900 ml of water at 75° C and then treated with silver oxide [prepared from 82 g (20% excess) of silver nitrate]. All iodide ions were removed within 20 minutes. After a further 10 minutes, the mixture was filtered, the filter-cake washed with ethanol/water (1:1) and the washings were combined with the filtrate and evaporated in vacuo. The residue was then heated for 0.5 hour at 120° C/0.2 mm Hg to yield 116 g of a syrup [94.4% yield; assumed 0.381 mol] which was a crude mixture of the bases obtained according to part A of Example 1.

B. The process:

116 g of the syrup obtained according to part A of this Example were dissolved in 950 ml of absolute tetrahydrofuran and 1600 ml of liquid ammonia. 17.5 g (2 × 0.381 mol) of sodium were added in small pieces during 15 to 20 minutes. Addition of a further 0.5 g of sodium gave a permanent blue colour. After 10 minutes, the mixture was decomposed with 60 g (1.5 equivalents) of ammonium chloride and the ammonia allowed to evaporate. The solid was then filtered off and the filtrate evaporated in vacuo. The solid and evaporation residue were re-combined and treated with water and then 800 ml of petroleum ether. The ethereal solution was dried and passed through a column containing 200 g of alumina; the latter was then washed with more petroleum ether. Evaporation of the eluates followed by distillation yielded 84.6 g (72.5%) of 1-(2-dimethylaminoethyl)-1,2,6,7-tetrahydro-2-methylindolo-[1,7-ab][1]benzazepine as a pale-yellow syrup of boiling point ca 148° C/$10^{-4}$ to $10^{-5}$ mm Hg.

84.6 g (0.276 mol) of 1-(2-dimethylaminoethyl)-1,2,6,7-tetrahydro-2-methylindolo[1,7-ab][1]benzazepine in 423 ml of dry benzene were treated with 33 ml (25% excess) of ethyl chloroformate under slight cooling. The mixture was then boiled at reflux for 16 hours. Thin layer chromatography indicated only partial reaction and the solution was therefore extracted with 0.5-N hydrochloric acid until all unreacted base was removed, the neutral benzene layer being stored. The acid extract was made alkaline, extracted with benzene and the extract evaporated to yield 49 g of the recovered base, 1-(2-dimethylaminoethyl)-1,2,6,7-tetrahydro-2-methylindolo[1,7-ab][1]benzazepine. The latter was redissolved in 245 ml of benzene, treated with 25.4 ml of ethyl chloroformate and boiled for 24 hours. The solution was again extracted with 0.5-N hydrochloric acid and the neutral benzene layer again stored. The acid extract was processed as before to yield 9 g of recovered base which were again treated with ethyl chloroformate as described earlier and then extracted with 0.5-N hydrochloric acid. The three neutral benzene extracts were combined, washed with water and dried. Evaporation yielded 92.2 g of a viscous syrup which was assumed to be the urethane, 1-[2-(N-ethoxycarbonyl-N-methylamino)-ethyl]-1,2,6,7-tetrahydro-2-methylindolo[1,7-ab][1]benzazepine (91.7% yield).

92.2 g (0.253 mol) of the urethane were autoclaved for 8 hours at 150° C with a solution of 50 g [3 equivalents at 85% concentration] of potassium hydroxide in 50 ml of water and 450 ml of ethanol. The solution obtained was then evaporated in vacuo, treated with ether and water and the ether extracted several times with 0.5-N hydrochloric acid. The acid extracts were combined, made alkaline with ammonia and extracted with ether. Evaporation of the ether extract yielded a residue which was distilled to give 64.4 g (81.7% yield) of pale-yellow, syrupy trans-1,2,6,7-tetrahydro-2-methyl-1-(2-methylaminoethyl)indolo[1,7-ab][1]benzazepine (boiling point 144°–152° C/$10^{-4}$ to $10^{-5}$ mm Hg) whose hydrochloride melted at 198°–200° C.

EXAMPLE 3

A. Preparation of the starting material:

22.8 g (0.075 mol) of 1,2,3,4,4a,8,9,14a-octahydro-3-ethylpyrido[4',3':2,3]indolo[1,7-ab][1]benzazepine were boiled under reflux for 24 hours with 200 ml of benzene and 16 ml (excess) of ethyl iodide. The resulting crude ethiodide was ground up under ether to yield 32.9 g (95.3%) of material.

In the same manner as described in part A of Example 2, HOFMANN elimination was carried out on the ethiodide using 329 ml of ethanol, 329 ml of water and a portion of silver oxide [obtained from 30.3 g of silver nitrate]. 21.3 g (89.8%) of an undistilled syrupy product were obtained which consisted mainly of 1-(2-diethylaminoethyl)-1,2,6,7-tetrahydro-2-methyleneindolo[1,7-ab][1]benzazepine together with some 1-(2-diethylaminoethyl)-6,7-dihydro-2-methylindolo[1,7-ab][1]-benzazepine.

B. The process:

21.3 g (0.064 mol) of the syrupy degradation product obtained according to part A of this Example were reduced using 213 ml of tetrahydrofuran, 426 ml of ammonia and 3 g (2 equivalents) of sodium in the same manner as described in part B of Example 2. 15.3 g (71.5% yield) of syrupy 1-(2-diethylaminoethyl)-1,2,6,7-tetrahydro-2-methylindolo[1,7-ab][1]benzazepine were obtained which distilled at 140° C (air-bath temperature )/2 × $10^{-5}$ mm Hg and whose oxalate melted at ca 155° C.

10.9 g (0.0326 mol) of 1-(2-diethylaminoethyl)-1,2,6,7-tetrahydro-2-methylindolo[1,7-ab][1]benzazepine were deethylated using ethyl chloroformate in a similar manner to that described in part B of Example 2, except that toluene was used as the solvent instead of benzene.

11.3 g (0.0298 mol) of the urethane, 1-[2-(N-ethoxycarbonyl-N-ethylamino)-ethyl]-1,2,6,7-tetrahydro-2-methylindolo[1,7-ab][1]benzazepine obtained after three successive treatments with ethyl chloroformate, were autoclaved for 8 hours at 140° C with a solution of 5.9 g [3 equivalents] of potassium hydroxide in 5.9 ml of water and 53 ml of ethanol. The resulting mixture was worked up as described in part B of Example 2 to yield the basic product, together with some unhydrolysed urethane which was given a second treatment with alkali. The combined basic products were distilled to give 5.9 g (64.7% yield) of pale-yellow, syrupy trans-1-(2-ethylaminoethyl)-1,2,6,7-tetrahydro-2-methylindolo[1,7-ab][1]benzazepine (boiling point 140° C [air-bath temperature]/2 × $10^{-5}$ mm Hg) whose hydrochloride melted at 169°–171° C.

EXAMPLE 4

A. Preparation of the starting material:

61.3 g (0.25 mol) of N-amino-iminodibenzyl hydrochloride were stirred in 250 ml of ethanol and treated with 31.8 g (0.25 mol) of 1,3-dimethyl-4-piperidone. The mixture was boiled under reflux for 1 hour, cooled to 55° C and then treated with 167 ml (0.5 mol) of 3-N ethanolic hydrogen chloride. The mixture was boiled with stirring for 0.5 hour, filtered and the filtrate evaporated. The residue obtained was combined with the filter-cake material and treated with water and ether. Some insoluble matter was filtered off and then the acidic aqueous layer was made alkaline and extracted with ether. The extract was washed, dried and evaporated. The residue was distilled to yield 36.5 g of the crude base 6,7-dihydro-2-methyl-1-(2-methylaminoethyl)-indolo[1,7-ab][1]benzazepine of boiling point ca 160° C/$10^{-4}$ mm Hg.

For purification, the 6,7-dihydro-2-methyl-1-(2-methylaminoethyl)-indolo[1,7-ab][1]benzazepine was converted into the hydrochloride by dissolving in ethanol and treating with ethanolic hydrogen chloride. After a first crop of 28.6 g of the hydrochloride was obtained, the liquors no longer crystallised and were converted back into the base by shaking with an excess of ammonia and ether. The base was re-distilled and again treated with ethanolic hydrogen chloride to yield a second crop of 2 g of the hydrochloride. The two crops were combined and recrystallised from ethanol to give 27.9 g (38.4% yield) of 6,7-dihydro-2-methyl-1-(2-methylaminoethyl)-indolo[1,7-ab][1]benzazepine hydrochloride of melting point 210°–212° C. The pure hydrochloride was now suspended in water and shaken out with an excess of ammonia and ether to yield the pure base 6,7-dihydro-2-methyl-1-(2-methylaminoethyl)-indolo[1,7-ab][1]benzazepine as a pale-yellow viscous syrup of boiling point ca 160° C (air-bath temperature)/$10^{-5}$ mm Hg.

B. The process:

7.4 g (0.0255 mol) of 6,7-dihydro-2-methyl-1-(2-methylaminoethyl)-indolo[1,7-ab][1]benzazepine were dissolved in 74 ml of tetrahydrofuran (freshly distilled from sodium) and 148 ml of liquid ammonia and reduced with 1.17 g (2 × 0.0255 mol) of sodium. Addition of a further 0.12 g (10% excess) of sodium caused formation of a permanent blue colour. After decomposition with 3 g of ammonium chloride, the mixture was worked up in the manner described in part B of Example 2. The basic product was distilled at ca 150° C (air-bath temperature)/$10^{-5}$ mm Hg to give the trans-1,2,6,7-tetrahydro-2-methyl-1-(2-methylaminoethyl)-indolo[1,7-ab][1]benzazepine whose hydrochloride melted at 198°–200° C.

EXAMPLE 5

A. Preparation of the starting material:

A mixture of 4.9 g (0.02 mol) of N-aminoiminodibenzyl hydrochloride, 1.8 g (0.025 mol) of methyl ethyl ketone and 20 ml of ethanol was boiled under reflux for 1 hour. The mixture was filtered while still warm and then evaporated in vacuo. The residue was treated with water and ether and the ethereal layer was washed, dried and evaporated. The product was distilled at ca 150° C (air-bath temperature)/$10^{-4}$ mm Hg (2.9 g; 58.6% yield) and recrystallised from light petroleum to give 2.4 g of 6,7-dihydro-1,2-dimethylindolo[1,7-ab][1]benzazepine of melting point 76°–77° C.

2.34 ml (1.5 × 0.0085 mol) of 5.4-N ethanolic dimethylamine was added, below the surface and with cooling, to 13.6 ml of glacial acetic acid. 0.95 ml (1.5 × 0.0085 mol) of a 40% formaldehyde solution were also added, followed by 2.1 g (0.0085 mol) of 6,7-dihydro-1,2-dimethylindolo[1,7-ab][1]benzazepine. The mixture was heated for 7 hours at 90° C, evaporated in vacuo and taken up in water and ether. The ether was separated and extracted with 2-N hydrochloric acid. The combined acid/aqueous extracts were made alkaline and extracted with ether. The latter ether extract was evaporated and distilled at ca 130° C (air-bath temperature)/$10^{-4}$ mm Hg to give 1.8 g (69.5% yield) of 1-(2-dimethylaminoethyl)-6,7-dihydro-2-methylindolo[1,7-ab][1]benzazepine whose oxalate melted at 154°–155° C.

B. The process:

The 1-(2-dimethylaminoethyl)-6,7-dihydro-2-methylindolo[1,7-ab][1]benzazepine obtained according to part A of this Example could be reduced using sodium/ammonia and demethylated using ethyl chloroformate/alkali in either sequence to yield the trans-1,2,6,7-tetrahydro-2-methyl-1-(2-methylaminoethyl)-indolo[1,7-ab][1]benzazepine [boiling point 144°–152° C/$10^{-4}$ to $10^{-5}$ mm Hg] in the same manner as described in part B of Example 2. The hydrochloride melted at 198°–200° C.

The following Example illustrates a typical pharmaceutical preparation containing one of the indolobenzazepine derivatives provided by this invention.

EXAMPLE A

Tablets weighing 155 mg and containing 25 mg of active ingredient are produced in the usual manner using the following ingredients:

| | |
|---|---|
| trans-1,2,6,7-Tetrahydro-2-methyl-1-(2-methylaminoethyl)-indolo[1,7-ab][1]benzazepine | 25.0 g |
| Lactose | 125.0 g |
| Talc | 4.0 g |
| Magnesium stearate | 1.0 g |

I claim:
1. A compound of the formula

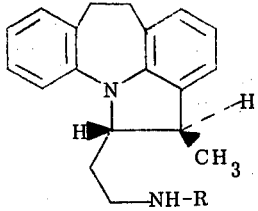

wherein R is selected from the group consisting of methyl and ethyl,
and the acid addition salts thereof.

2. The compound: trans-1,2,6,7-tetrahydro-2-methyl-1-(2-methylaminoethyl)-indolo[1,7-ab][1]benzazepine.

3. The compound: trans-1-(2-ethylaminoethyl)-1,2,6,7-tetrahydro-2-methylindolo[1,7-ab][1]benzazepine hydrochloride.

4. A compound of the formula

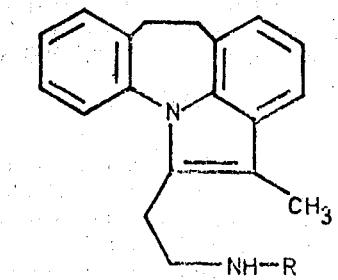

II wherein R is selected from the group consisting of methyl and ethyl.

5. A compound of the formula

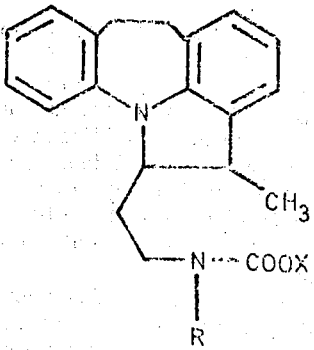

X wherein R is selected from the group consisting of methyl and ethyl and X is a lower alkyl group.

* * * * *